United States Patent [19]
Sakurai et al.

[11] Patent Number: 4,580,441
[45] Date of Patent: Apr. 8, 1986

[54] DIESEL SMOKE METER

[75] Inventors: Takashi Sakurai; Hiroshi Mizuno, both of Nagoya; Shigeyuki Akita; Masao Kodera, both of Okazaki; Kunihiko Sasaki, Nukata, all of Japan

[73] Assignees: Nippondenso Co., Ltd., Kariya; Nippon Soken, Inc., Nishio, both of Japan

[21] Appl. No.: 608,196

[22] Filed: May 8, 1984

[30] Foreign Application Priority Data

May 10, 1983 [JP] Japan .................. 58-81520
Jul. 6, 1983 [JP] Japan .................. 58-122583
Sep. 19, 1983 [JP] Japan .................. 58-172616

[51] Int. Cl.$^4$ .......................................... G01M 15/00
[52] U.S. Cl. ........................................ 73/28; 250/250; 324/71.4
[58] Field of Search .............. 73/28, 432 PS; 250/250, 250/428; 60/276, 277; 324/71.4

[56] References Cited

U.S. PATENT DOCUMENTS 4,501,138 2/1985 McCandless .................. 73/116

FOREIGN PATENT DOCUMENTS 11840 1/1983 Japan .................. 250/250

Primary Examiner—Jerry W. Myracle
Attorney, Agent, or Firm—Cushman, Darby & Cushman

[57] ABSTRACT

A diesel smoke meter which uses micro-waves to detect the density of black smoke contained in the exhaust gas discharged from the diesel engine through an exhaust pipe. A micro-wave transmitting device is coupled to the exhaust pipe and transmits micro-waves into the exhaust pipe. Micro-waves transiting the exhaust pipe are attenuated by the black smoke in the exhaust gas. A micro-wave receiving device receives the attenuated micro-waves and provides a received signal which varies in accordance with the signal level of the attenuated micro-waves. A measuring device receives the received signal and provides an output indicative of the density of black smoke in the exhaust gas.

16 Claims, 22 Drawing Figures

DIESEL SMOKE METER

BACKGROUND OF THE INVENTION

The present invention relates to a Diesel smoke meter which measures an amount of carbon contained in exhaust gases of the Diesel engine to find a density of black smoke.

In view of resource conservation as well as public safety, it is necessary to detect black smoke discharged from the Diesel engine to maintain the combustion of the engine in an optimum condition. It has been eagerly desired to develop a compact smoke meter which is high in precision and is suitably mounted on a vehicle.

As a smoke meter of this kind, it has been heretofore known to use a photo-system wherein light emitted from a light source is transmitted into the exhaust gas or reflected therein, and the amount of carbon in the exhaust gas is measured by the intensity of transmitted light or reflected light received by a light receiving means.

However, in the photo-system smoke meter just described, there arises the problem that when carbon particles adhere to the light source, the accuracy of the light receiving means or windows which are provided in the exhaust gas pipe line to transmit light, deteriorates. To prevent this problem, it has been necessary to spray clean air against the window or to perform maintenance frequently.

SUMMARY OF THE INVENTION

One object of the present invention is to provide a Diesel smoke meter which can detect with accuracy the density of black smoke contained in the exhaust gas discharged from the Diesel engine and can withstand such use for a long period of time.

Another object of the present invention is to provide a Diesel smoke meter which is free from the detection accuracy deterioration due to the adherence of carbon particles which form the carbon smoke.

Still another object of the present invention is to provide a Diesel smoke meter which uses micro-waves as a detecting medium.

More than 90% of black smoke comprise carbon components. On the other hand, it is known that a radio wave is absorbed by the carbon particles. According to the experiments conducted by the inventors, such absorprion is noticeable in a micro-wave zone where frequency is more than 1000 MHz as shown in FIG. 1. In FIG. 1, a line x indicates the case where a large amount of carbon particles are present, and a line y indicates the case where a small amount of carbon particles are present.

The inventors have noticed, in addition to the above-descrived fact, that micro-waves have a high transmissive force which transmits through the adhered carbon as compared with light, and thus the deterioration of the detecting accuracy due to the adherence of carbon particles will not occur.

The Diesel smoke meter in accordance with the present invention comprises a micro-wave transmitting means for transmitting micro-waves into an exhaust pipe of the engine, a micro-wave receiving means for receiving said micro-waves (attenuated by black smoke flowing through the exhaust pipe while the micro-waves are transmitted through the exhaust pipe) to provide receiving signals corresponding to the receiving intensity of the micro-waves, and a measuring means for detecting the density of black smoke in accordance with a signal level of said receiving signal.

The aforesaid micro-wave transmitting means comprises a micro-wave transmitter, and a transmitting waveguide for introducing the micro-waves transmitted from the transmitter into said exhaust pipe. The aforesaid micro-wave receiving means comprises a receiving waveguide for delivering the micro-waves which have transversely propagated through the exhaust pipe, and a micro-wave detector for receiving the thus delivered micro-waves. A micro-wave transmissive window formed of a micro-wave transmissive material is provided on a connecting portion between each of the waveguides and the exhaust pipe.

The above-described transmitting waveguide and receiving waveguide can be replaced with a micro-wave transmitting antenna and a micro-wave receiving antenna, respectively, which are projected into a micro-wave resonance cavity formed within the exhaust pipe and connected to a micro-wave receiver and a micro-wave detector, respectively.

Also, the above-described transmitting waveguide and receiving waveguide can be replaced with a micro-wave transmission path comprising two conductors one end of which is connected to the micro-wave transmitter and the other end of which is connected to the micro-wave detector.

DESCRIPTION OF THE PREFERRED EMBODIMENTS

In the following, the present invention will be described by way of illustrated embodiments.

Figure 1:
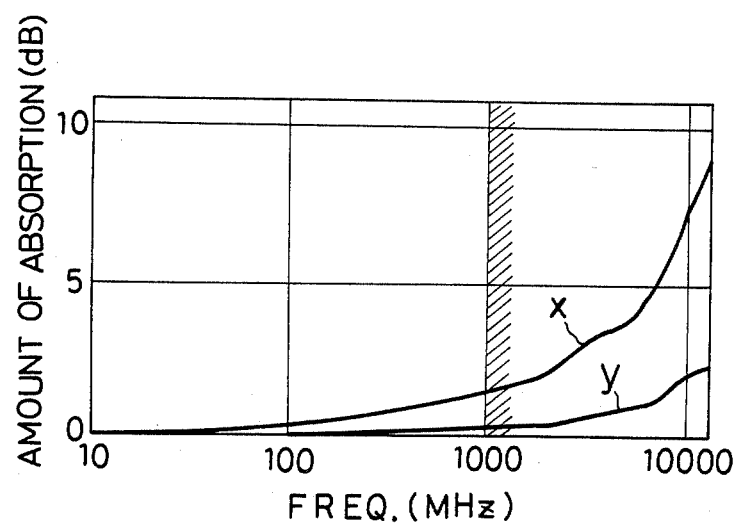
FIG. 1 is a view showing the characteristics of frequencies of radio waves absorbed by carbon particles.
Figure 2:
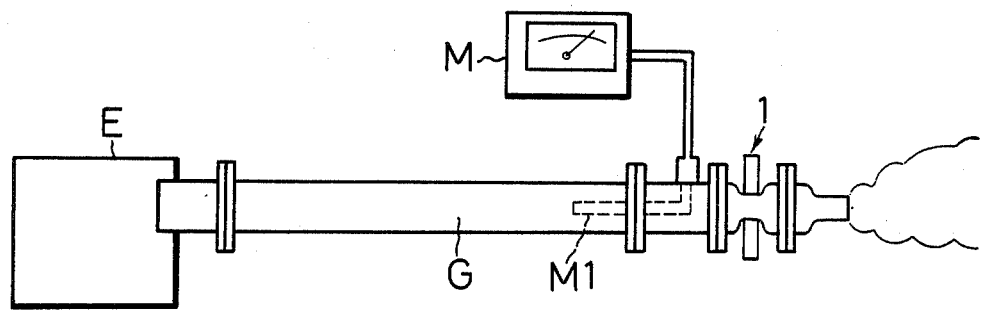
FIGS. 2 to 8 show a first embodiment of the present invention, FIG. 2 being a view showing the construction of an engine exhaust experimenting device, FIG. 3 being a fragmentary sectional plan view of a smoke meter, FIG. 4 being a sectional view taken on line IV—IV of FIG. 3, FIG. 5 being a circuit diagram of the receiving circuit, FIG. 6 being a view showing changes by lapse of time of the receiving signals in accordance with the change in time of the density of black smoke, FIG. 7 being a view showing the change in level of the receiving signal with respect to the density of the black smoke, and FIG. 8 being a view showing the degree that the output of the receiving signal is lowered due to the increase in adhered carbon by lapse of time comparing the smoke meter of the present invention with the photo-system smoke meter.
Figure 3:
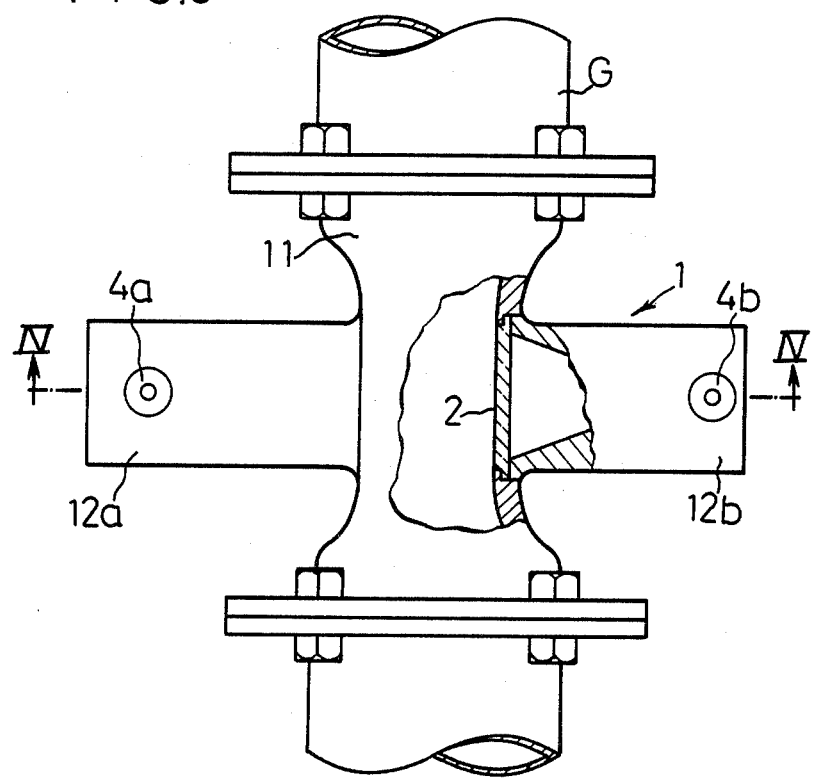

FIGS. 2 through 8 show a first embodiment of the present invention. FIG. 2 shows the construction of the exhaust experimenting device of the engine provided with a Diesel smoke meter in accordance with the present invention. In FIG. 2, reference character E designates a 4-cylinder 2200 cc Diesel engine. A smoke meter 1 of the present invention is connected by a flange to a portion in the vicinity of the end of an exhaust pipe G extending from the engine E. Upstream of the smoke meter 1 is positioned a sampling probe M1 of a filter type smoke meter made by Bosch Company in West Germany, to provide a Bosch Smoke No. which indicates the density of black smoke. The smoke meter 1 comprises, as shown in FIG. 3, a cylindrical portion 11 having opposite open ends with connecting flanges, and a transmitting waveguide 12a and a receiving waveguide 12b which are connected to opposed side walls of the cylindrical portion 11.

Figure 4:
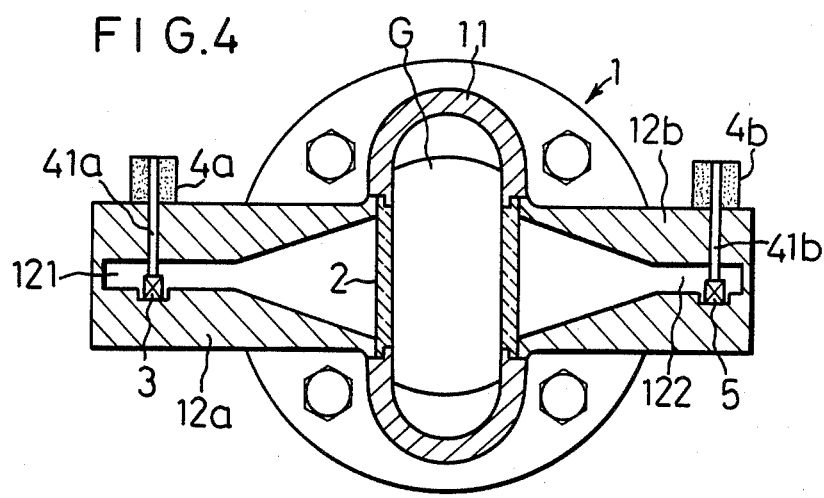

The cylindrical portion 11 is connected by the flanges to the exhaust pipe G to form a part of the pipe. The cylindrical portion 11 has an intermediate portion in the form of an elliptical configuration, in section, as shown in FIG. 4, and has the waveguides 12a and 12b connected to the opposed side walls thereof. The waveguides 12a and 12b are in the form of a cylinder, one end of which is closed, an inner surface thereof being spread into a tapered shape directed towards an opening, and a spread open end being joined into a hole formed in the side wall of the cylindrical portion 11. An opening of the waveguides 12a and 12b is provided with a microwave transmissive window 2 formed of heat-resistant glass to prevent entry of carbon or the like into the waveguides 12a and 12b. It is noted that the transmissive window 2 permits the transmission of the microwaves with little attenuation.

A micro-wave transmitting Gunn diode 3 is disposed in a resonance cavity 12 formed in a closed end within the waveguide 12a. The Gunn-diode 3 has a negative pole connected to and energized with a body of the waveguide 12a, and a positive pole to which is connected a center electrode 41a suspended from a coaxial plug 4a provided on the upper portion of the waveguide 12a.

On the other hand, a schottkey barrier diode 5 for detecting the micro-waves is disposed within a resonance cavity formed in the closed end within the waveguide 12b, the diode 5 having a negative pole connected to and energized with a body of the waveguide 12b, and a positive pole which is connected to a center electrode 41b suspended from an axial plug 4b provided on the upper portion of the waveguide 12b.

A coaxial cable extending to a power source (not shown) is connected to the coaxial plug 4a. Also, a coaxial cable extending to a receiving circuit 6, shown in FIG. 5, is connected to the coaxial plug 4b.

Figure 5:
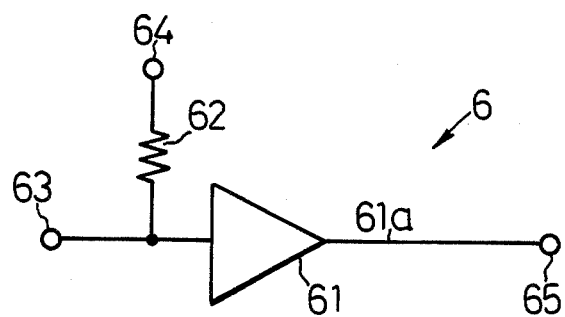

In FIG. 5, reference numeral 61 designates a DC amplifier, and 62 a bias current setting resistor for the diode 5. A terminal 63 is an input terminal, to which is connected a coaxial cable from the coaxial plug 4b (see FIG. 3). Terminals 64, 65 are a power source terminal and an output terminal, respectively.

The output terminal 65 is connected to a measuring means (not shown), the measuring means detecting the density of black smoke in accordance with a voltage level of a received signal 61a released from the DC amplifier 61.

Operation of the smoke meter 1 having the construction as described above will be described hereinafter.

The Gunn-diode 3, with a predetermined voltage applied from the unshown power source through the center electrode 41a, transmits micro-waves (23.8 GHz in the illustrated embodiment). The micro-waves are transmitted through the waveguide 12a and reach the other waveguide 12b across the cylindrical portion 11 and are received and detected by the Schottkey barrier diode 5. The diode 5 produces a current opposite in polarity to that of the bias current in accordance with the intensity of the received micro-waves whereby a potential of the input terminal 63 of the receiving circuit 6 is lowered.

Now, the micro-waves which are transmitted through the cylindrical portion 11 are absorbed and attenuated by the carbon particles within the black smoke passing through the cylinder. Thus, if the black smoke is high in density, the strength of the microwaves reaching the diode 5 decreases, whereas if the smoke is low in density, the strength of the received micro-waves increases. Accordingly, in case of the former, the potential of the input terminal 63 of the receiving circuit 6 rises, whereas in case of the latter, it lowers.

Figure 6:
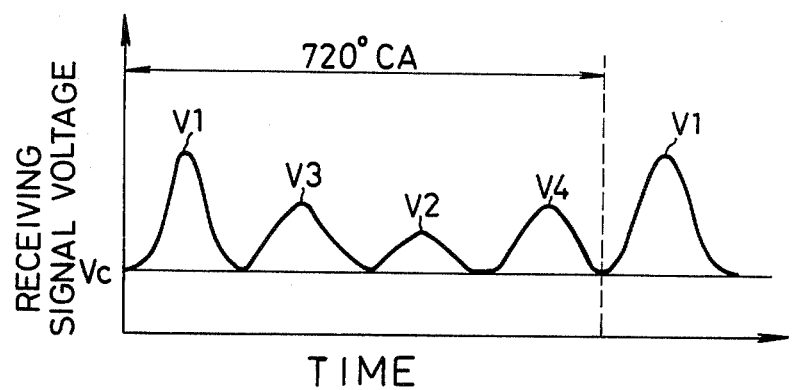

Here, FIG. 6 shows a received signal 61a appearing in the output terminal 65 of the receiving circuit 6. As shown, the received signal 61a pulsates with an increase in amount of black smoke in the exhaust gas pipe G resulting from combustion and explosion in each cylinder. Voltage pulsations V1, V2, V3 and V4 in the figure respectively correspond to the first to fourth cylinders. According to this figure, the first cylinder has the largest amount of smoke whereas the second cylinder has the least. In FIG. 6, Vc indicates the meter output voltage where no discharge of black smoke is present.

Figure 7:
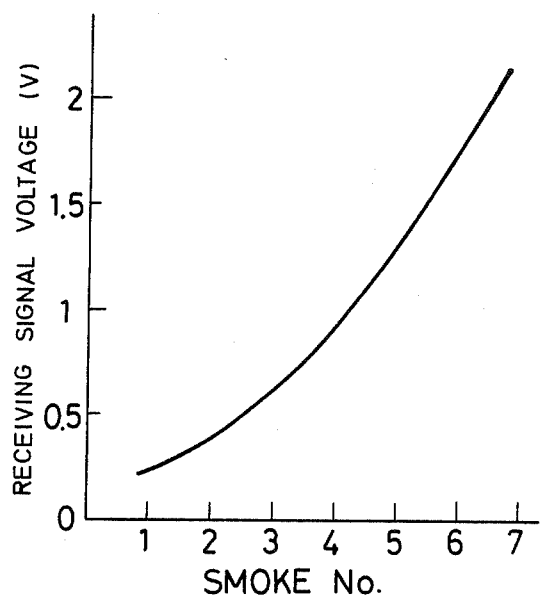

FIG. 7 shows the state wherein the signal voltage V1 corresponding to the first cylinder of the engine changes relative to the change in density of black smoke. As can be seen from FIG. 7, the above-described voltage V1 primarily rises as the density of black smoke rises, namely, the Bosch Smoke No. increases.

When the density is measured, the carbon particles adhere to the transmissive window 2. However, unlike the light, the micro-waves are somewhat absorbed by the adhered carbon but may reach the detecting diode 5 with sufficient strength. Adherence of carbon particles rarely increases after it reaches a given amount, and therefore, if an arrangement is made so that an influence caused by the adhered carbon is cancelled by the receiving signal 61a, it is possible to accurately measure the amount of carbon in the exhaust gas.

Figure 8:
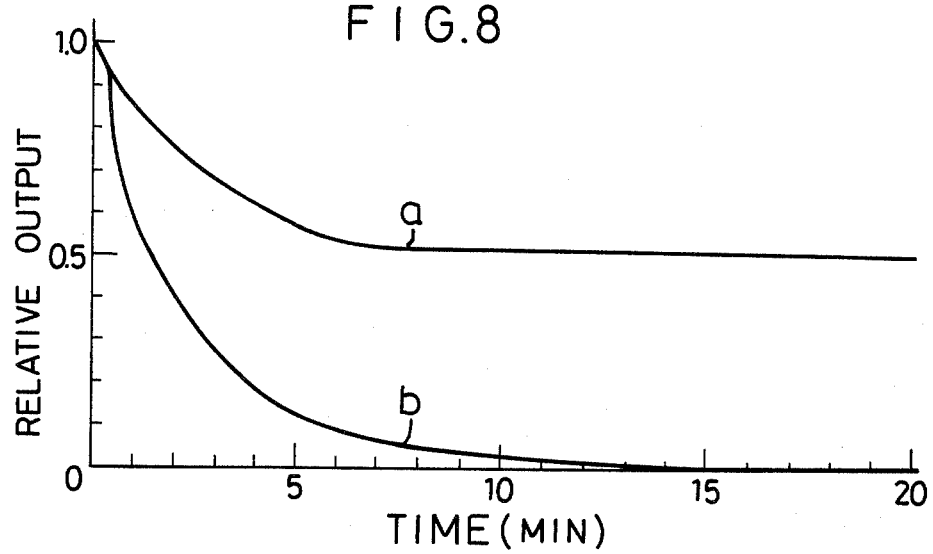

FIG. 8 shows the results of an experiment which proves the above-described fact. FIG. 8 shows the change (by lapse of time) of outputs of the smoke meter in accordance with the present invention (line a in the figure) and the photo-system smoke meter (line b in the figure), respectively, where the black smoke of the density of Bosch Smoke No. 4 is permitted to flow. According to this, in the photo-system smoke meter, when the carbon particles are adhered to the light transmissive window 2, the detecting function rapidly decreases.

Moreover, if micro-waves are used, the transmissive window 2 need not be transparent. Therefore, if a Teflon coating is applied to the internal surfaces of the transmissive window 2, it is possible to minimize the amount of carbon adhered thereto.

Moreover, since micro-waves are merely absorbed and attenuated by the carbon, the micro-waves will not at all react with so-called white smoke which principally comprises HC, and only the density of black smoke is measured with accuracy.

As described above, the present invention provides a Diesel smoke meter which uses micro-waves for measurement, has high accuracy, is compact, and requires no trouble in maintenance.

Figure 9:
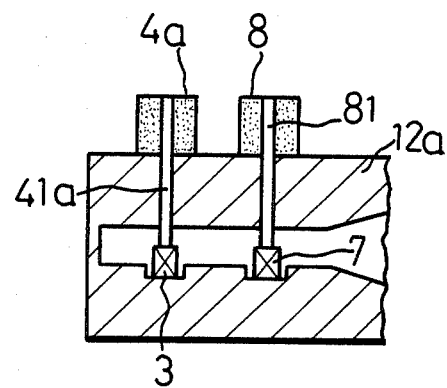
FIG. 9 is a fragmentary sectional view showing a further embodiment of the micro-wave receiving waveguide.
Figure 10:
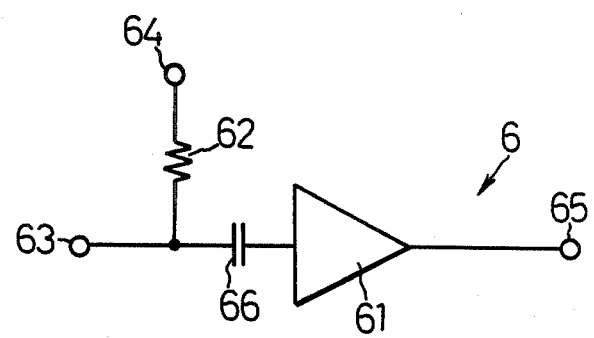
FIG. 10 is a circuit diagram showing a further embodiment of the receiving circuit.

It will be noted in the above-described embodiment that a PIN diode 7 is provided frontwardly of the Gunn-diode 3, the diode 7 is subjected to switching in a predetermined period through a center electrode 81 extending from a coaxial plug 8 to chop the micro-waves transmitted from the Gunn-diode 3, the chopped microwaves are received by the Schottkey barrier diode 5, (FIG. 9), and an amplifier 61 is provided for amplification through an AC coupling capacitor 66 of the receiving circuit 6 shown in FIG. 10. According to this arrangement, a DC fluctuating portion (such as drift) can be removed to provide measurement with higher accuracy.

Moreover, in the above-described embodiment, a part of the micro-waves transmitted from the Gunn-diode 3 is removed by means of a power distributor to monitor the strength of the transmitted micro-waves, and this is compared with the strength of the received micro-waves received by the Schottkey barrier diode 5, to obtain an attenuation percentage of the micro-waves. Thereby it is possible to effect measurements of high accuracy, independent of a micro-wave power source variation.

Figure 11:
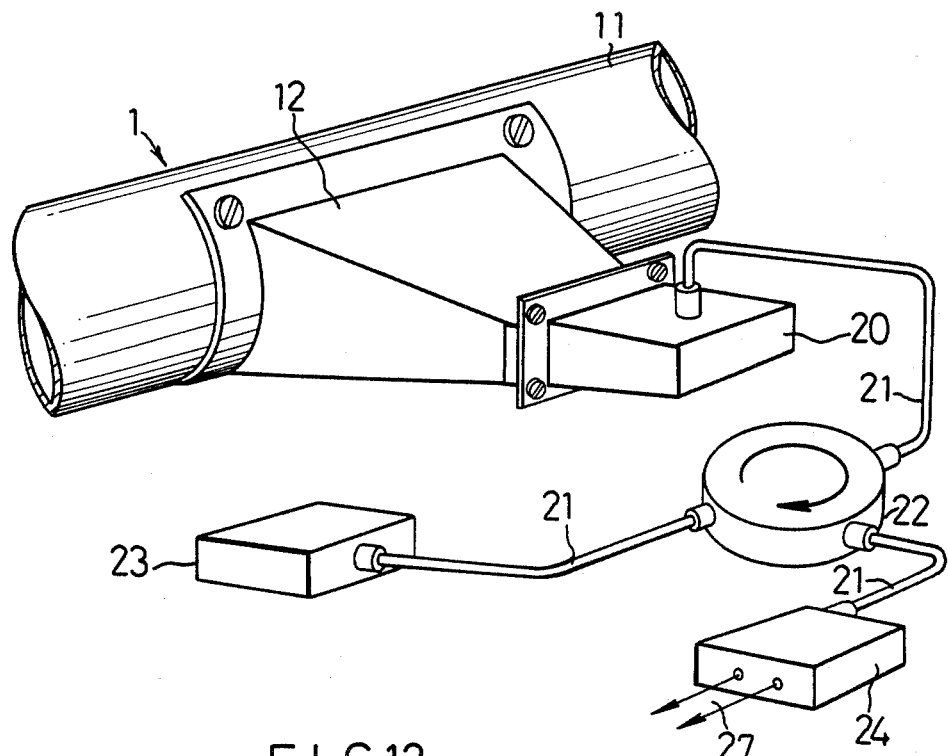
FIGS. 11 through 14 show a second embodiment of the present invention, FIG. 11 being a perspective view of the whole construction of the smoke meter, FIG. 12 being a sectional view of the same, FIG. 13 being a sectional view of the micro-wave transmitter, and FIG. 14 being a sectional view of the micro-wave detector.
Figure 12:
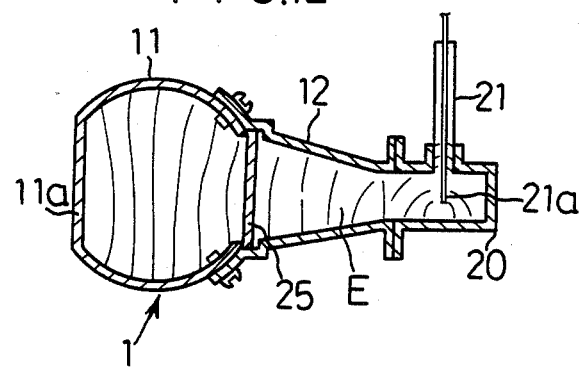

FIGS. 11 through 14 show a second embodiment of the present invention. In FIGS. 11 and 12, one end of a receiving and transmitting micro-wave waveguide 12, formed in a tapered fashion on its side walls is connected to the cylindrical portion 11 of the smoke meter 1. A side wall of cylindrical portion 11 opposed to the side walls on which is connected a waveguide 12, serves as a reflecting surface 11a for micro-waves. A coaxial-to-waveguide converter 20 is connected to the other end of the waveguide 12, and an inner conductor 21a of a coaxial cable 21 is projectingly provided within the converter 20 to serve as a micro-wave transmitting antenna. The coaxial cable 21 extends to a micro-wave transmitter 23 and a micro-wave transmitting antenna. The coaxial cable 21 extends to a micro-wave transmitter 23 and a micro-wave detector 24 via a circulator 22. The waveguide 12 is provided at one end with a micro-wave transmissive window 25 formed from a ceramic plate which can prevent entry of smoke and permits micro-waves to be transmit therethrough.

Figure 13:
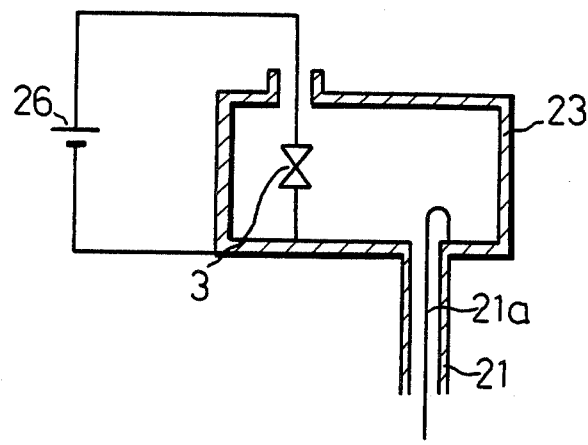

FIG. 13 shows the construction of a micro-wave transmitter 23. A voltage is applied to the Gunn-diode 3 from a power source 26, and the micro-waves transmitted from the diode 3 are transmitted through a coaxial cable 21 connected to a casing of a transmitter 23, which casing forms a resonance cavity.

Figure 14:
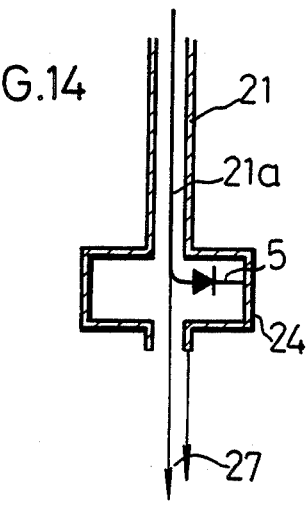

FIG. 14 shows the construction of a micro-wave detector 24. A Schottkey barrier diode 5 is disposed within a casing of the detector 24, a positive pole thereof being connected to an inner conductor 21a of a coaxial cable 21 connected to the casing with the negative pole being connected to the casing body. The micro-waves transmitted within the coaxial cable 21 are rectified and detected by the diode 5, and a DC signal obtained therefrom is fed to the receiving circuit 6 (FIG. 5) shown in the first embodiment via a lead wire 27.

Now, the micro-waves transmitted from the micro-wave transmitter 23 are fed to the converter 20 via a circulator 22 and projected into the waveguide 12. The micro-waves form a pulsating electric field, as shown at E in FIG. 12, which propagates within the waveguide 12 and reaches the cylindrical portion 11. The micro-waves are then reflected by the reflecting surface 11a and are reciprocated within the cylindrical portion 11, after which they are again fed to the circulator 22 from the waveguide 12, and are then transmitted to a micro-wave detector 24. During the reciprocation within the cylindrical portion 11, the micro-waves are absorbed and attenuated by carbon particles of black smoke flowing through the cylindrical portion 11.

Even by the construction according to the just-discussed embodiment, an effect similar to that of the above-described first embodiment can be provided and the micro-wave are reciprocated within the exhaust gas thereby enhancing the detecting sensitivity.

It will be noted that a material used for the transmissive window in the first and second embodiments is not limited to heat-resisting glass or ceramic, but any material which is excellent in heat resistance and has a micro-wave transmissivity can be also used.

Figure 15:
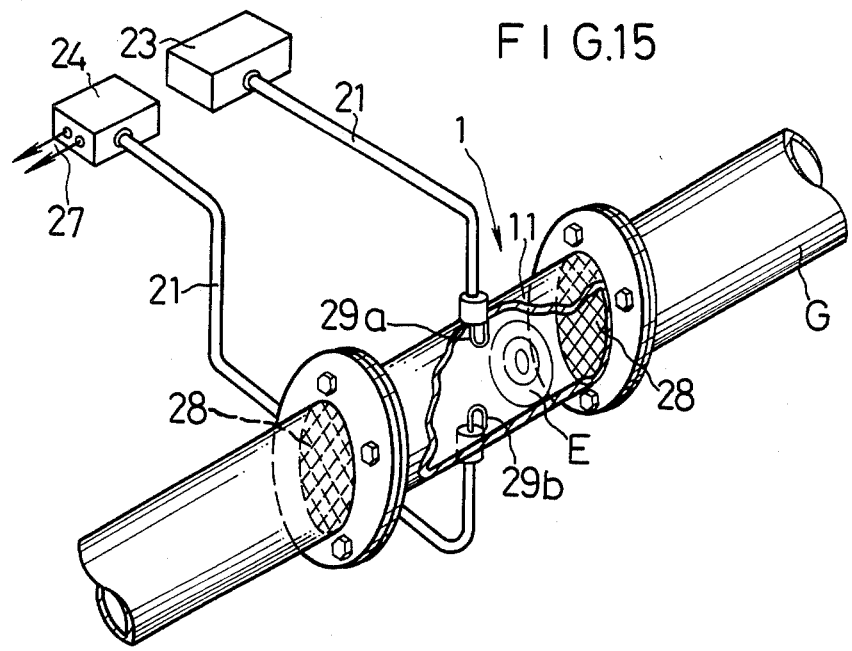
FIG. 15 is a fragmentary sectional perspective view of the smoke meter showing a third embodiment.

FIG. 15 shows a fifth embodiment of the present invention. A wire net 28 having predetermined meshes, which form a partitioning plate, is interposed between connecting flanges formed on opposite openings of the cylindrical portion 11 of the smoke meter 1, and connecting flanges of the exhaust gas pipe G. In the wire net 28, the size of the meshes is designed so as to have the cut-off frequencies high enough to permit the exhaust gas to flow freely but not to permit the micro-waves used for measurement to pass therethrough. Thereby, the cylindrical portion 11 forms a micro-wave resonance cavity surround by the pair of wire nets 28 and the cylindrical wall. The cylindrical wall is provided with a transmitting loop antenna 29a for transmitting micro-waves into the cylindrical portion, and a receiving loop antenna 29b for receiving micro-waves which are resonance-amplified within the cylinder. The transmitting antenna 29a is connected to a micro-wave transmitter 23 by means of a coaxial cable 21 whereas the receiving antenna 29b is connected to a micro-wave detector 24. The transmitter 23 and detector 24 have the same construction as that of the above-described second embodiment.

The micro-waves transmitted from the micro-wave transmitter 23 are transmitted into the cylindrical portion 11 from the antenna 29a to form a pulsating electric field, as shown at E in the figure, and are resonance-amplified. Incidentally, when carbon particles are present in the exhaust gas flowing through the cylinder, the micro-waves are absorbed and attenuated thereby and their resonance strength is lowered materially in accordance with the amount of carbon. Thus, the density of black smoke can be known from the degree of attenuation of the micro-waves received by the antenna 29b.

As described above, even by the construction as in the present embodiment, it is possible to obtain the effect similar to that of the first embodiment, and to utilize the resonance cavity to enhance the detecting sensitivity.

It will be noted in the present embodiment that an antenna can be a rod-like antenna, and a position of installation thereof is not limited to the opposed position as shown. The cylindrical portion need not be cylindrical, and the partitioning plate does not always comprise the wire net 28 as long as it cuts off the micro-waves and permits the exhaust gas to flow.

Figure 16:
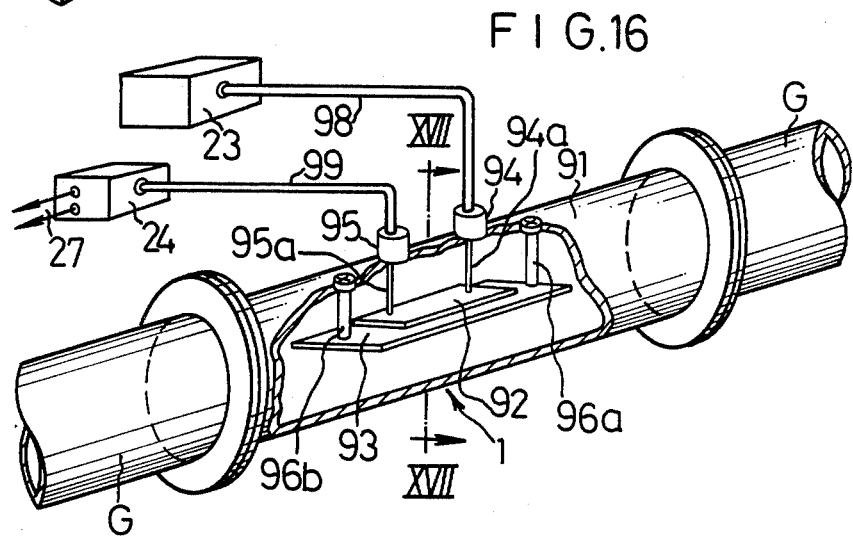
FIGS. 16 through 18 show a fourth embodiment, FIG. 16 being a fragmentary sectional perspective view of the smoke meter, FIG. 17 being a sectional view taken on line XVII—XVII of FIG. 16, and FIG. 18 being an electric equivalent circuit of the smoke meter.
Figure 17:
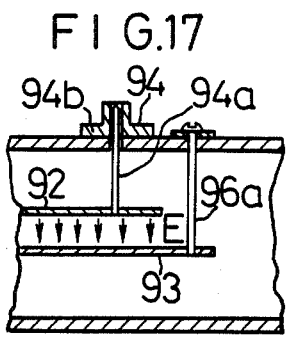

FIGS. 16 and 17 show a fourth embodiment of the present invention. In FIG. 16, the cylindrical portion 11 is interiorly provided with two opposed metal plates 92 and 93 which are parallel to a flow of the exhaust gas.

Connected to opposite ends of the metal plate 92 are inner conductors 94a, 95a extending from coaxial plugs 94, 95 provided on the cylindrical wall of the cylindrical portion 11, whereby the metal plate 92 is supported within the cylindrical portion 11. The metal plate 93 is energized and supported on the cylindrical wall of the cylindrical portion 11 by means of metal rods 96a, 96b connected to opposite ends thereof. It is noted that an outer conductor 94b (only the plug 94 is shown in FIG. 17) of the plugs 94, 95 is energized with the cylindrical wall.

A coaxial cable 98 extending to a micro-wave transmitter 23 is connected to the plug 94, and a coaxial cable 99 extending to a micro-wave detector 24 is connected to the plug 95.

The micro-waves transmitted from the transmitter 23 reach the plug 94 via the coaxial cable 98 and are transmitted between the metal plate 92 (connected to the inner conductors 94a, 95a) and the metal plate 93 (connected to the external conductor) while forming the electric field E as shown in FIG. 17. The micro-waves reaching the plug 95 are inputted into the detector 24 via the coaxial cable 99, and the detector 24 provides an output signal in accordance with the strength of micro-waves reaching the detector 24. The output signal is fed to the receiving circuit 6 (FIG. 5) by a lead wire 27.

The micro-waves transmitted between the metal plates 92 and 93 are absorbed and attenuated by the carbon particles in the exhaust gas flowing therebetween. Thus, the strength of the micro-waves reaching the detector 3 is lowered in accordance with the amount of carbon in the exhaust gas, and the output signal of detector 3 changes. In this manner, it is possible to accurately measure the density of the carbon in the exhaust gas.

During the measurement, carbon adheres to the metal plates 92, 93 and the like, and the micro-waves are somewhat absorbed by the adhered carbon, but the measurement is not affected thereby, which is different from the case where light is used. Further, if a Teflon coating is applied to the metal plates 92, 93 and the like, it is possible to minimize the amount of adhered carbon.

Moreover, the measured values are not at all affected by the grain size of dust or speed of the exhaust gas.

Figure 18:
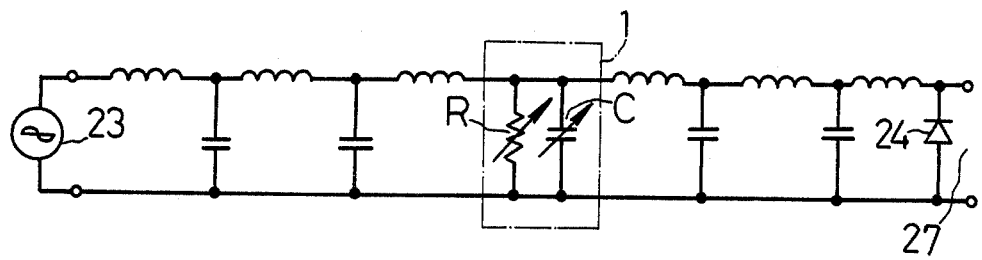

FIG. 18 shows an equivalent circuit of a micro-wave transmission line in the present invention. Resistance portion R and capacity portion C vary during transmission with variations in density of carbon in the exhaust gas.

Figure 19:
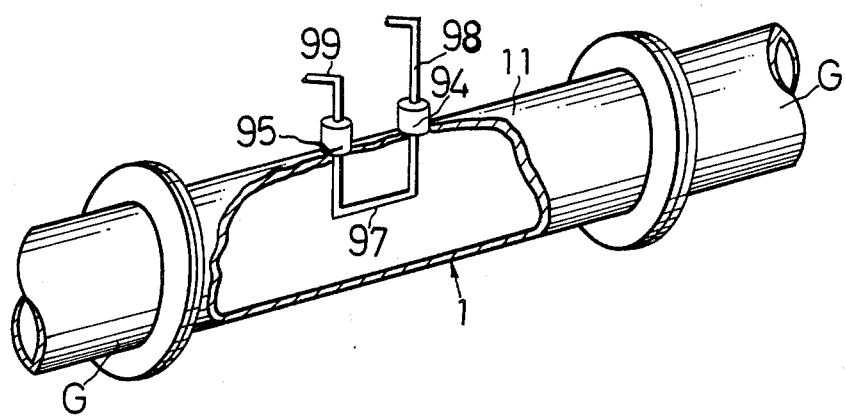
FIG. 19 is a fragmentary sectional perspective view of the smoke meter showing a fifth embodiment of the present invention.

FIG. 19 shows a fifth embodiment. A metal rod 97 is disposed on the center of the cylindrical portion 11, and both ends of the metal rod 97 are bent and connected to the inner conductors of the coaxial plugs 94, 95, respectively. The cylindrical wall of the cylindrical portion 11 is energized with the outer conductors of the plugs 94, 95 to thereby constitute a coaxial waveguide with a metal rod 97 being a center conductor and with the cylindrical wall being an external conductor. The micro-waves entering through coaxial cable 98 are transmitted within the coaxial waveguide which also serves as an exhaust gas flow-passage, and during such transmission, the micro-waves are absorbed and attenuated by the carbon.

Figure 20:
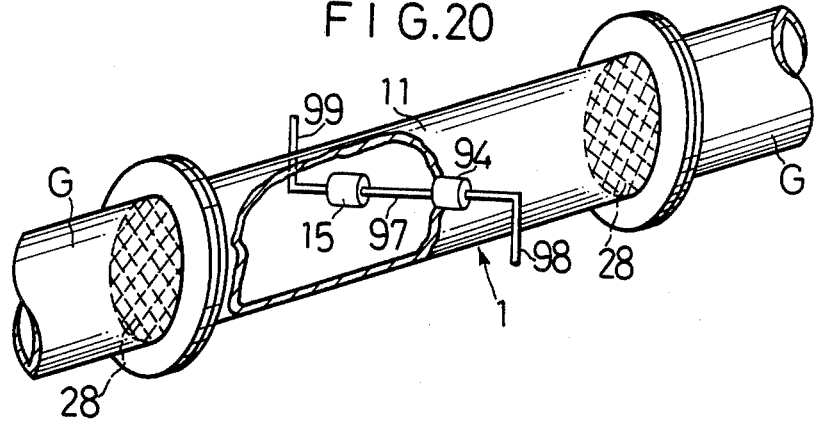
FIG. 20 is a fragmentary sectional perspective view of the smoke meter showing a sixth embodiment.

FIG. 20 shows a sixth embodiment of the present invention. The coaxial plugs 94, 95 are provided opposedly on the cylindrical wall of the cylindrical portion 11, and the cylindrical portion is interiorly provided with a metal rod 97 which is disposed transverse within the cylindrical portion, said metal rod 97 having both ends thereof connected to the inner conductors of the plugs 94, 95. Both openings of the cylindrical portion 11 are covered with wire nets 28 which are partitioning plates. The wire net has size enough to permit the exhaust gas to flow therethrough without preventing passage of the micro-waves. The cylindrical wall of the cylindrical portion 11 is energized with the outer conductors of the plugs 94, 95. Thereby, there is formed a coaxial waveguide with the metal rod 97 being a center conductor and with the wire net 28 and cylindrical portion 11 being the external conductors.

Even the just-described embodiment has the effect smililar to that of the above-described fifth embodiment.

Figure 21:
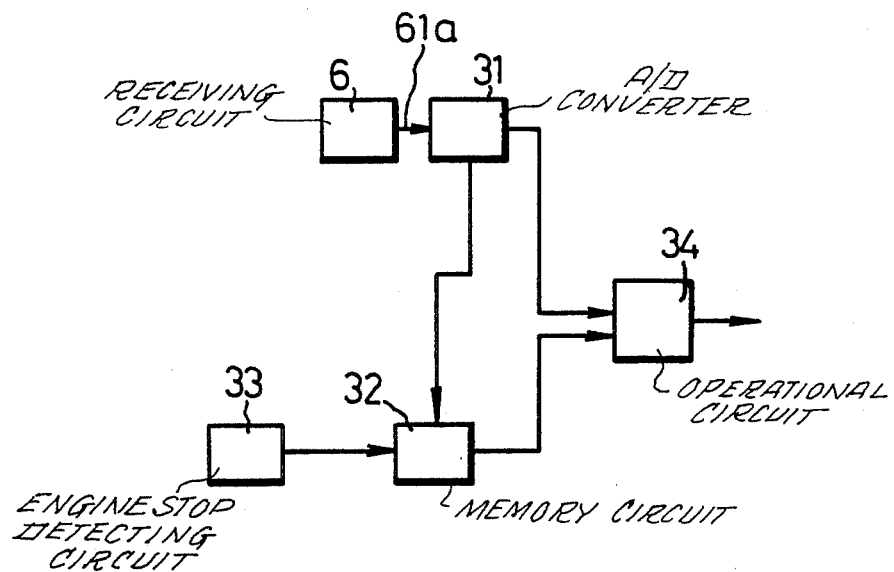
FIGS. 21 and 22 show a seventh embodiment of the present invention, FIG. 21 being a block diagram showing the circuit construction of the receiving means, and FIG. 22 being a view showing the change (by lapse of time of the receiving signal in accordance with the change in time) of the density of the black smoke.
Figure 22:
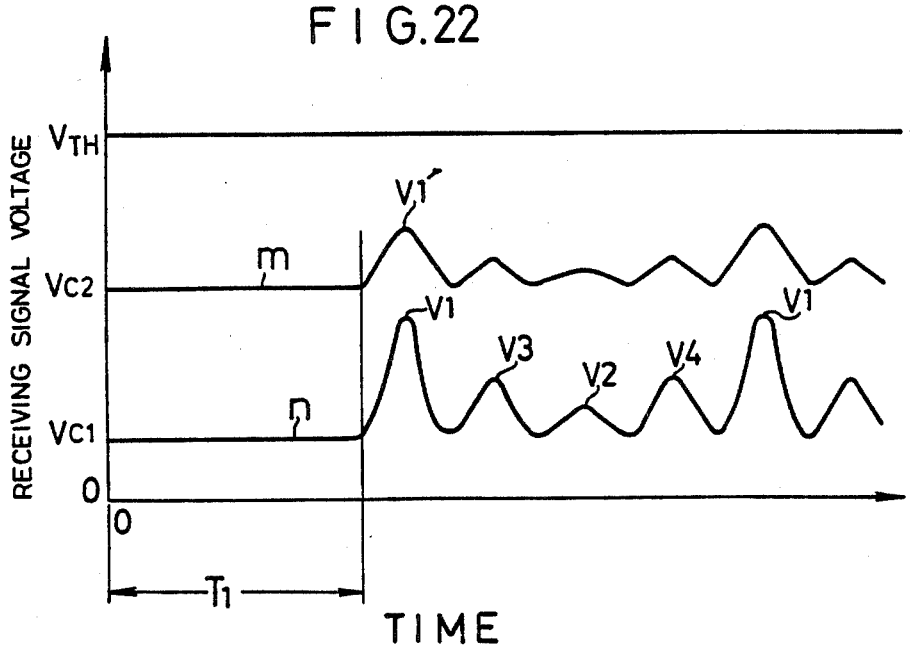

FIGS. 21 and 22 show a seventh embodiment of the present invention. In this embodiment, the measuring means comprises an A/D converter 31, a memory circuit 32, an engine stop detecting circuit 33 and an operational circuit 34. The aforesaid detecting circuit 33 detects the stop of the engine, for example, by the non-energizing condition of the fuel supplying magnet valve of a fuel injection pump.

The received signal 61a provided by the receiving circuit 6 (FIG. 5) varies with the amount of black smoke flowing through the exhaust pipe G, as described in connection with the first embodiment. This will be again shown in FIG. 22 (a line n in the figure). In the figure, $V_{TH}$ indicates a voltage level of the received signal 61a where no micro-wave is received, and during the time $T_1$ the engine is not started and thus the black smoke does not flow through the exhaust pipe G.

During the stoppage of the engine, a stop detection signal is provided from the detecting circuit 33 and the memory circuit 32 is operated. At that time, the A/D converter 31 provides a digital value $D_1$ which is proportional to a differential voltage $(V_{TH}-V_{C1})$, the digital value $D_1$ being stored as a reference value in the memory circuit 32.

When the first cylinder is exhausted after the engine has been started, the signal voltage is V1, and the A/D converter circuit 31 provides a digital value $D_2$ proportional to the differential voltage $(V_{TH}-V1)$. An operational circuit 34 calculates the ratio $D_2/D_1$.

When the carbon is adhered to the transmissive window 2, even in the event the black smoke does not flow through the exhaust pipe G, the micro-waves are absorbed and attenuated by the adhered carbon. Thus, in this case, the received signal 61a is at the voltage $Vc_2$ which is higher than voltage $Vc_1$ at the time $T_1$, as indicated at line m in the figure, and pulsates with the voltage $Vc_2$ being a reference value after the engine has been started. Thereby, even if the amount of carbon in the exhaust gas is the same, the received signal 61a, for example, when the first cylinder is exhausted, will be a voltage $V1'$ higher than the voltage $V1$.

In this case, when the engine is stopped, a digital value $D_1'$, proportional to the differential voltage ($V_{TH} - Vc_2$), is stored as an initial value into the memory circuit 32, in a procedure similar to that previously described, and during the operation of the engine, the ratio $D_2'/D_1'$ between the initial value $D_1'$ and a digital value $D_2'$ proportional to a differential volatage ($V_{TH} - V1'$), is calculated by the operational circuit 34.

The initial value $D_1'$ and digital value $D_2'$ decrease at the same rate relative to the increase in the adhered amount of carbon. Thus, the ratio $D_2'/D_1'$ depends on the amount of carbon in the exhaust gas flowing through the exhaust pipe G. That is, if the amount of carbon in the exhaust gas is the same, the ratios $D_2/D_1$ and $D_2'/D_1'$ are always equal to each other irrespective of the amount of carbon adhered to the measuring window 2. The more the amount of carbon in the exhaust gas, the smaller the ratios $D_2/D_1$ and $D_2'/D_1'$.

As described above, if the change of the ratio between a signal level of the received signal 61a when black smoke does not flow and a signal level of the received signal 61a when black smoke flows is known, it is possible to accurately measure the amount of carbon in the exhaust gas, that is, the density of black smoke.

What is claimed is:

1. A diesel smoke meter for detecting a density of black smoke contained in the exhaust gas discharged from a diesel engine, comprising:

an exhaust pipe for discharging the exhaust gas;

micro-wave transmitting means for transmitting into said exhaust pipe microwaves subject to being attenuated by black smoke;

micro-wave receiving means for receiving, during transmission of said micro-waves through said exhaust pipe, said micro-waves as attenuated by black smoke and for providing a received signal in accordance with the received strength of said micro-waves; and measuring means for detecting the density of black smoke from a signal level of said received signal.

2. A diesel smoke meter as claimed in claim 1, wherein said micro-wave transmitting means includes a micro-wave transmitter and a transmitting waveguide for introducing the micro-waves transmitted from said micro-wave transmitter into said exhaust pipe, and wherein said micro-wave receiving means includes (a) a receiving waveguide for delivering the micro-waves passing through and propagated within said exhaust pipe, and (b) a micro-wave detector for receiving the delivered micro-waves.

3. A diesel smoke meter as claimed in claim 2, wherein one end of said transmitting waveguide and one end of said receiving waveguide are respectively connected to at least one side of said exhaust pipe, said exhaust pipe having at least one micro-wave transmissive window formed of a micro-wave transmissive material, said at least one window being formed at a connection between said exhaust pipe and said one end of said transmitting waveguide and said one end of said receiving waveguide.

4. A diesel smoke meter as claimed in claim 3, wherein said at least one window includes first and second micro-wave transmissive windows, and wherein both said first and second micro-wave transmissive windows are symmetrically positioned on opposite sides of said exhaust pipe, and wherein said one end of said micro-wave transmitting waveguide and said one end of said micro-wave receiving waveguide are respectively connected at these symmetrical opposite positions.

5. A diesel smoke meter as claimed in claim 2, wherein said micro-wave transmitting waveguide and said micro-wave receiving waveguide comprise a single micro-wave waveguide.

6. A diesel smoke meter as claimed in claim 5, wherein said single micro-wave waveguide has one end connected to a side of said exhaust pipe and the other end connected to said micro-wave transmitter and said micro-wave receiver through a circulator.

7. A diesel smoke meter as claimed in claim 5, wherein said exhaust pipe includes a micro-wave transmissive window of a micro-wave transmissive material formed at a connection between said exhaust pipe and said single micro-wave waveguide.

8. A diesel smoke meter as claimed in claim 2, wherein said micro-wave transmitter includes a resonance cavity formed within the transmitting waveguide, and a micro-wave transmitting Gunn-diode provided within said resonance cavity.

9. A diesel smoke meter as claimed in claim 8, wherein a PIN diode is provided within said transmitting waveguide for chopping micro-waves transmitted from said Gunn-diode, said receiving means being provided with a coupling capacitor.

10. A diesel smoke meter as claimed in claim 2, wherein said micro-wave detector includes a resonance cavity formed in the receiving waveguide, and a micro-wave detecting Schottkey barrier diode provided within said resonance cavity.

11. A diesel smoke meter as claimed in claim 1, wherein said micro-wave transmitting means includes a micro-wave transmitter and a micro-wave transmitting antenna connected thereto, said transmitting antenna projecting into said exhaust pipe, and wherein said micro-wave receiving means includes a micro-wave detector and a micro-wave receiving antenna connected thereto, said receiving antenna projecting into said exhaust pipe, said exhaust pipe serving as a micro-wave resonance cavity defined by partitioning plates opposedly disposed within said exhaust pipe in predetermined spaced relation in a flowing direction of exhaust gas, said plates each having a number of holes through which black smoke may flow but micro-waves may not pass, said micro-wave transmitting antenna and said micro-wave receiving antenna being positioned within said resonance cavity.

12. A diesel smoke meter as claim in claim 1, wherein said exhaust pipe is interiorly provided with a micro-wave transmission line comprising two conductors, the micro-wave transmitting means being connected to one end of said transmission line and the micro-wave receiving means being connected to the other end thereof.

13. A diesel smoke meter as claimed in claim 12, wherein said micro-wave transmission line includes an electric conductive flat plate provided within the exhaust pipe.

14. A diesel smoke meter as claimed in claim 12, wherein said micro-wave transmission line includes an electrically conductive cylindrical body which forms a part of the exhaust pipe, and an electrically conductive axial member disposed substantially colinear with a central, longitudinal axis of said cylindrical body.

15. A diesel smoke meter as claimed in claim 12, wherein said micro-wave transmission line includes an electrically conductive cylindrical body which forms a part of the exhaust pipe, partitioning plates transversely disposed in said exhaust pipe and having a number of small holes through which black smoke may flow but micro-waves may not pass, and an electrically conductive axial member disposed transversely across said cylindrical body.

16. A diesel smoke meter as claimed in claim 1, wherein said measuring means includes a memory circuit for storing, as a reference level, a signal level of said received signal when black smoke does not flow, and an operational circuit for calculating a ratio between said signal level of said received signal when black smoke flows and said reference level.

* * * * *